United States Patent [19]

Bartholmes et al.

[11] Patent Number: 5,798,253
[45] Date of Patent: Aug. 25, 1998

[54] METHOD OF CULTURING MICRO-ORGANISMS UNDER A MUTAGENIC INFLUENCE

[75] Inventors: Peter Bartholmes, Witten; Michael Kaufmann, Dortmund; Thomas Schwarz, Leichlingen, all of Germany

[73] Assignee: Bitop Gesellschaft für Biotechnische Optimierung mbH, Witten, Germany

[21] Appl. No.: 704,749

[22] PCT Filed: Mar. 1, 1995

[86] PCT No.: PCT/EP95/00752

§ 371 Date: Oct. 29, 1996

§ 102(e) Date: Oct. 29, 1996

[87] PCT Pub. No.: WO95/23845

PCT Pub. Date: Sep. 8, 1995

[30] Foreign Application Priority Data

Mar. 2, 1994 [DE] Germany .................... 44 06 343.3
Mar. 1, 1995 [DE] Germany .................... 195 07 103.4

[51] Int. Cl.$^6$ ................ C12N 1/00; C12N 1/36; C12N 1/20
[52] U.S. Cl. .......... 435/243; 435/245; 435/262; 435/821; 435/822; 435/813; 435/819
[58] Field of Search .................. 435/243, 813, 435/819, 42, 245, 262, 822, 821

[56] References Cited

U.S. PATENT DOCUMENTS 4,391,887 7/1983 Baumgarten et al. .............. 435/42

FOREIGN PATENT DOCUMENTS 2665180 1/1992 France .
4124900 3/1992 Germany .
2010327 6/1979 United Kingdom .
2247012 7/1990 United Kingdom .

*Primary Examiner*—Leon B. Lankford, Jr.
*Assistant Examiner*—Christopher R. Tate
*Attorney, Agent, or Firm*—Collard & Roe, P.C

[57] ABSTRACT

An accelerated micro-organism culture method is for decomposing harmful substances. For this purpose, the cultivation, mutagenic treatment and stabilization of the micro-organisms are carried out simultaneously in a mutation fermenter containing a nutrient-rich basic medium (basic medium 1); selection is carried out in a selection fermenter containing a basic medium which is low in nutrients and is enriched with the harmful substance (basic medium 2); small amounts of biomass released from the nutrient-rich basic medium (basic medium 1) of the mutation fermenter are continuously removed from the mutation fermenter and transferred to the selection fermenter. Small amounts of biomass released from the basic medium which is low in nutrients (basic medium 2) of the selection fermenter are removed from the selection fermenter and transferred to the mutation fermenter. The entire process is carried out continuously in alternating selection and mutation phases, in the manner of a repeated cycle. The mutation fermenter and the selection fermenter are associated with computerized control circuits by means of which the fermentation parameters can be adjusted independently of one another in both fermenters.

8 Claims, 1 Drawing Sheet

METHOD OF CULTURING MICRO-ORGANISMS UNDER A MUTAGENIC INFLUENCE

BACKGROUND OF THE INVENTION

1. Field of the Invention

The invention relates to a method of culturing micro-organisms that are suitable for the degradation of certain harmful substances, by which method existing micro-organisms are cultured in a growth-promoting nutritive solution, subjected to chemically and/or physically mutagenically acting influences, stabilized under growth-promoting conditions, and selected under the influence of the harmful substances under growth-limiting conditions, whereby said selected micro-organisms are returned to the start of the process.

2. The Prior Art

The use of micro-organisms for the biological degradation of harmful substances finds important application in the restoration of old materials, as well as in the purification of waste waters and air, in connection with which the harmful substances are decomposed by the micro-organisms, or converted into other substances, whose disposal is less problematic. Micro-organisms suitable for the efficient biological degradation of harmful substances must have, beyond the specific capability of degradation, an optimal harmful substance tolerance, the highest possible division rate, as well as genetic stability.

For culturing bacteria mutants capable of degrading harmful substances, DE 41 24 900 A1 discloses a method by which the bacteria are cultured under conditions not limiting the growth, subject to a mutation-producing UV-radiation, and the mutated bacteria are then brought together with the harmful substance under conditions limiting the growth. If necessary, the micro-organisms could be transferred from the selection stage into a first reactor, in which they are stabilized in order to be subsequently subjected in the mutation stage to UV-radiation again.

However, it has been found that the method according to the state of the art is not suitable for developing micro-organism populations that are capable of degrading organic compounds and particularly complex compounds, because one or two mutagenic treatment do not suffice for obtaining within a reasonable time the establishment of a micro-organism population suitable for degrading complex organic compounds. This is, to begin with, a basically statistic problem, which with high probability is connected with the fact that for degrading complex organic harmful substances, several degradation reactions are required, which take place sequentially, and in which intermediate products are produced which, under certain circumstances, are more toxic for the micro-organisms than the starting product. Thus the composition of the selection medium changes in the course of time, so that the micro-organism population has to adapt itself time and again with respect to degradation capability and harmful substance tolerance. Such adaptation requires some time and causes the process to take a longer time, overall, and to thus become uneconomical.

Furthermore, the method known from the state of the art requires a considerable expenditure in terms of equipment, because the culturing, mutagenic treating and stabilizing of the micro-organism population is carried out in different reactors. Moreover, following stabilization in a nutrient-rich medium, the micro-organisms are directly transferred into the selection fermenter for inoculation with the selection medium containing the harmful substance. It may occur, for example, that the biomass subjected to selection still contains considerable proportions of nutritive substances, the latter having been introduced in the selection fermenter and adversely influencing the selection, as such nutritive substances are preferably used as a nutrient source by the micro-organisms. Therefore, the selection of micro-organisms degrading the harmful substances will start only once the introduced nutritive substances have been consumed. This, firstly, leads to positive selection of micro-organisms not capable of degrading the harmful substances, which results in an additional delay of the entire selection process.

SUMMARY OF THE INVENTION

Therefore, the object of the invention is to further develop the method of the type specified above in a way such that on the one hand, the culturing and the mutation remain exactly controllable under growth-promoting conditions, and the selection remains exactly controllable under growth-limiting conditions, on the other hand. The intention is to make it possible to channel with low equipment expenditure the natural evolution process as narrow and as controlled as possible in order to be able in this way to culture micro-organisms with the desired properties as quickly as possible.

For achieving this object, the invention proposes based on the method of the type specified above that the culturing, the mutagenic treatment and the stabilization are carried out simultaneously in a mutation fermenter containing a nutrient-rich basic medium;

the selection takes place in a selection fermenter containing a low-nutrient basic medium enriched with the harmful substance;

small amounts of biomass are continuously withdrawn from the mutation fermenter, relieved of the nutrient-rich basic medium of the mutation fermenter, and transferred into the selection fermenter;

small amounts of biomass are continuously withdrawn from the selection fermenter, relieved of the low-nutrient basic medium of the selection fermenter, and transferred into the mutation fermenter;

the entire process takes place continuously in the way of a repeating circulation in alternating selection and mutation phases;

whereby computer-controlled control circuits are associated with the mutation fermenter, on the one hand, and with the selection fermenter, on the other hand, by which the fermentation parameters are adjustable independently of each other in both fermenters.

The method according to the invention operates in a particularly advantageous way with a double fermenter system, in which the two principles of evolution—selection and mutation—can take place individually in an optimized way. In this connection, the micro-organisms are cultured in both fermenters which, in operation, inoculate each other, continuously in alternating selection and mutation phases. In the mutation fermenter, the mutation rate in the culture can be drastically increased through ultraviolet irradiation and/or through the addition of mutagenic chemicals, whereas in the selection fermenter, suitable conditions are provided for the suitable mutants in a controlled way, such conditions being suitable for the degradation of the harmful substance. The genetic variety of the micro-organism population is increased by repeated mutagenic treatments, so that said population is capable of adapting itself more rapidly with respect to the degradation capability and harmful substance tolerance if the conditions in the selection fermenter, thus the ratio of the amounts of intermediate products changes in the course of time. In this way, the development of the micro-organism population is, through the use of mutation and selection in a cyclic process, drastically accelerated versus the individual mutation or selection according to the state of the art.

Therefore, the method according to the invention makes it possible to generate or to specialize relatively quickly entire biocenobes in specially defined degradation capacities and/or tolerances. The benefits of the method lie in the quasi-natural reproduction of micro-organisms through a targeted, controlled evolution. As opposed to micro-organisms manipulated gene-technologically, this reduces the risk of producing revertants that became ineffective. The application of computer-controlled control circuits permits adjusting defined chemical and process-technical conditions i-n a reproducible way, and to find in this manner the optimal conditions for each of all individual processes.

According to a particularly advantageous implementation of the method according to the invention, provision is made that the selection fermenter (fermenter 2) operates toxin-statically, i.e., that the concentration of harmful substance remains constant in the course of the process. This, on the one hand, has the advantage the selection pressure is maintained constant over the entire process, so that only those micro-organisms can grow which exhibit the tolerance versus the harmful substance, or which are capable of degrading the harmful substance. On the other hand, there is the advantage that a biocenotic equilibrium adjusts itself more rapidly in the micro-organism population.

According to another preferred implementation of the invention, the selection fermenter (fermenter 2) operates turbidostatically. In this case, the selection process is controlled in the selection fermenter mainly via the biomass.

Preferably, the basic media of the biomass are exchanged when the biomass is transferred from one fermenter to the other. Such exchange of the basic media is usefully carried out in dialysis sections arranged between the fermenters. In this way, it is avoided that medium gets from one fermenter into the other, which would offer the micro-organisms nutrients that would be used preferred versus the harmful substances, which leads to a delay of the selection process. Furthermore, through careful adaptation to the new medium, which takes place in the dialysis section, the "lag" phase is reduced with each fermenter change, and the entire process is accelerated in this way. Another advantage lies in that by exchanging the medium between the selection and the mutation fermenters. UV-absorbing substances are removed, which are contained in the selection medium, or which have been produced within the framework of the microbial metabolism and separated into the medium, and which could reduce the mutation efficiency when using UV-radiation as the mutagen.

In a preferred implementation of the method according to the invention, the basic medium (basic medium 1) of the mutation fermenter (fermenter 1) contains the harmful substance to be degraded. The mutation fermenter usefully operates toxin-statically.

In another preferred implementation of the method according to the invention, the mutation fermenter (fermenter 1) operates turbido-statically.

BRIEF DESCRIPTION OF THE DRAWINGS

An exemplified implementation of the method according to the invention is explained in the following by reference to the attached drawing, which schematically shows the structure of an installation suitable for carrying out the process.

DETAILED DESCRIPTION OF PREFERRED EMBODIMENTS

Figure 1:
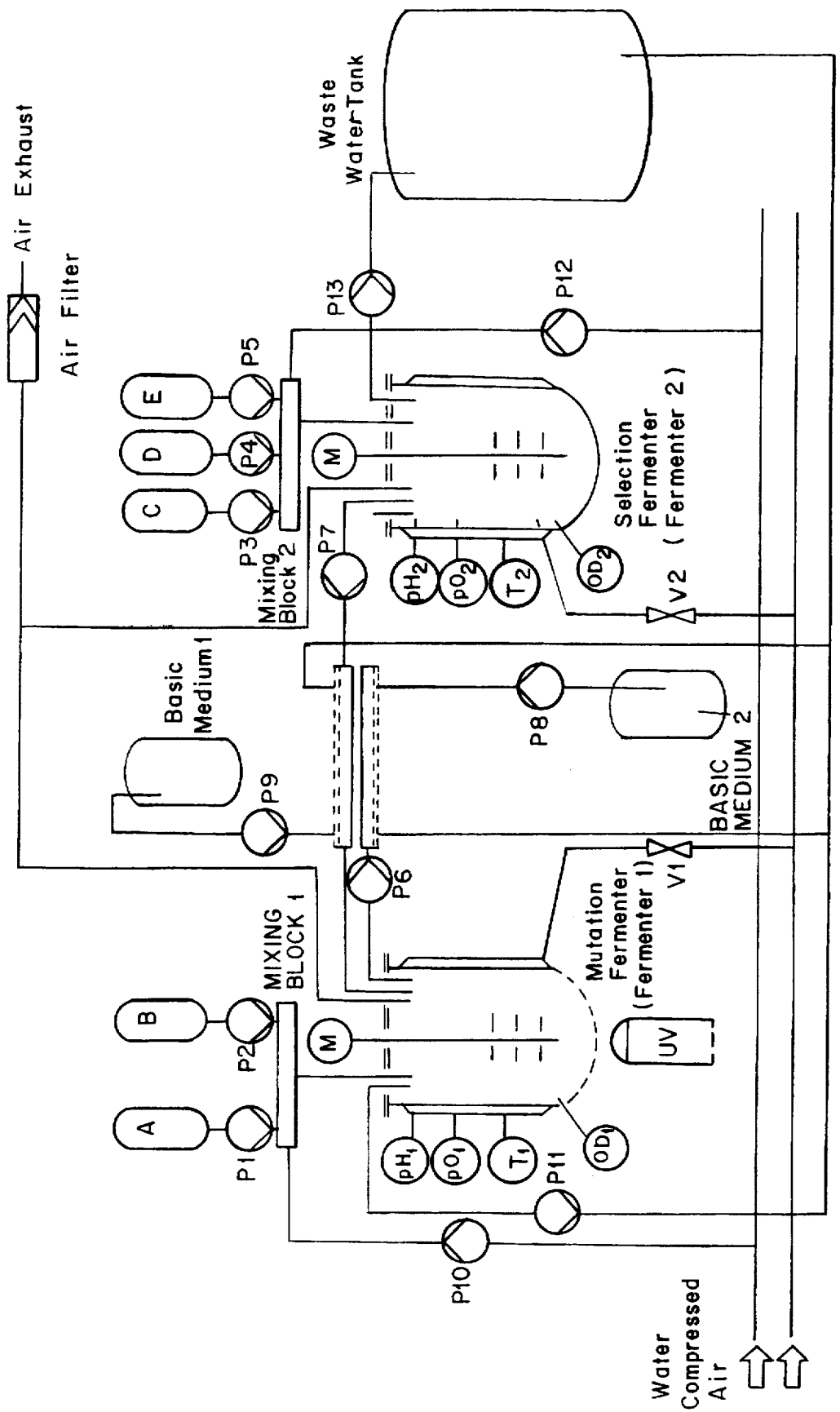

The installation shown in the drawing has two fermenter vessels with a holding capacity of one to two liters, which can be operated continuously, namely the mutation fermenter (fermenter 1) and the selection fermenter (fermenter 2). Both fermenters are equipped with the following standard sensorics: $pH_1$ and $pH_2$ for the pH-values; $pO_1$ and $pO_2$ for the oxygen contents. $T_1$ and $T_2$ for the temperature, and $OD_1$ and $OD_2$ for the optical density. In addition, suitable sensorics are in both fermenters or in the bypass of the two fermenters for detecting the actual toxin ("selection substrate") concentrations. The fermenter 2 can be continuously inoculated with micro-organisms from the fermenter 1 via a pump P6 and a dialysis section downstream, in which careful adaptation of the media is achieved. In the same way, the fermenter 1 is inoculated with micro-organisms from the fermenter 2 via a pump $P_7$ and a dialysis section downstream. The pumps $P_8$ and $P_9$ supply the dialysis sections with basic medium. In the dialysis sections, the micro-organisms to be transferred from the one or other fermenter are relived of the basic medium of the origin fermenter and enriched with the basic medium of the target fermenter.

The mutation fermenter (fermenter 1) has an irradiation capability by means of UV. The radiation passes through a quartz window. The fermenter 1 is supplied with medium via a mixing block 1, as well as via the pumps 10 (water), $P_1$ (medium concentrate) and $P_2$ (nutrient substrate). A pump $P_{11}$ assures a constant volume of the fermentation broth by pumping off into the waste water tank as required by the level.

The medium feed into the selection fermenter (fermenter 2) takes place via a mixing block 2 as well as via the pumps P (water), $P_3$ (medium concentrate), $P_4$ (nutrient substrate), and $P_5$ ("selection substrate"). A pump $P_{13}$ assures a constant volume of the fermentation broth by pumping off into a collecting tank as required by the level.

The system has a modular structure and permits the use of all types of different selection reactors.

All pumps are designed for continuous operation and controllable via suitable interfaces with a process control system. The waste water tanks each have a holding capacity of 200 liters. The introduction of air, the rotary speed of the agitator, the feed of base and acid and the tempering are self-controlled by the two fermenter systems and not via the process control system.

What is claimed is:

1. Method of culturing micro-organisms suitable for the degradation of a chemical compound by which existing micro-organisms are cultured in a growth-promoting nutritive solution, subjected to a mutagenic acting influence selected from the group consisting of a chemically acting influence, a physically acting influence, and chemically and physically mutagenic acting influences, stabilized under growth-promoting conditions, and selected under the influence of the chemical compound under growth-limiting conditions, in which said selected micro-organisms are returned to start of the process, comprising the steps of:

(a) carrying out the cultivation, mutagenic treatment and stabilization simultaneously in a mutation fermenter containing a nutrient-rich medium;

(b) having selection take place in a selection fermenter containing a low-nutrient medium enriched with the chemical compound;

(c) withdrawing biomass in small amounts from the mutation fermenter, and removing from the biomass the nutrient-rich medium of the mutation fermenter and transferring the biomass into the selection fermenter;

(d) withdrawing biomass in small amounts from the selection fermenter, and removing from the biomass the low-nutrient medium of the selection fermenter and transferring the biomass into the mutation fermenter;

(e) said method entirely taking place continuously by way of a repeating circulation in alternating selection phase and mutation phase; and (f) providing computer-controlled control circuits associated with the mutation fermenter, and with the selection fermenter for adjusting the fermentation parameters in both fermenters independently of one another.

2. Method according to claim 1, comprising operating the selection reactor toxin-statically.

3. Method according to claim 1, comprising operating the selection reactor turbidostatically.

4. Method according to claim 1, comprising during the transfer of biomass from one fermenter to the other, exchanging the medium of the biomass.

5. Method according to claim 4, comprising the exchanging of the medium is carried out in dialysis sections arranged between the fermenters.

6. Method according to claim 1, wherein the medium of the mutation fermenter contains the chemical compound to be degraded.

7. A Method according to claim 6, comprising operating the mutation fermenter toxin-statically.

8. The Method according to claim 6, comprising operating the mutation fermenter turbidostatically.

* * * * *